United States Patent
Trozera

(10) Patent No.: US 6,475,233 B2
(45) Date of Patent: *Nov. 5, 2002

(54) STENT HAVING TAPERED STRUTS

(75) Inventor: Thomas Trozera, Del Mar, CA (US)

(73) Assignee: Interventional Technologies, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 87 days.

(21) Appl. No.: 08/956,672

(22) Filed: Oct. 23, 1997

(65) Prior Publication Data

US 2001/0010014 A1 Jul. 26, 2001

Related U.S. Application Data

(63) Continuation-in-part of application No. 08/835,015, filed on Apr. 8, 1997.

(51) Int. Cl.$^7$ .................................................. A61F 2/06
(52) U.S. Cl. ..................................... 623/1.15; 623/1.14
(58) Field of Search ............................. 623/1, 12, 1.15, 623/1.14, 1.36; 606/194, 195, 108

(56) References Cited

U.S. PATENT DOCUMENTS

| | | |
|---|---|---|
| 4,733,665 A | 3/1988 | Palmaz |
| 4,739,762 A | 4/1988 | Palmaz |
| 4,776,337 A | * 10/1988 | Palmaz ........................... 623/1 |

(List continued on next page.)

*Primary Examiner*—Bruce Snow
(74) *Attorney, Agent, or Firm*—Vidas, Arrett & Steinkraus; Michael E. Kilpera, Esq.

(57) ABSTRACT

The present invention is directed to an expandable stent which is relatively flexible along its longitudinal axis to facilitate delivery through tortuous body lumens, but which is stiff and stable enough radially in an expanded condition to maintain the patency of a body lumen such as an artery when implanted therein. The struts of the present invention have a specific trapezoidal, triangular or a reduced radii configuration projecting radially outward that functions to reduce the forces necessary to penetrate the vessel wall thereby minimizing trauma or damage imparted to the wall during deployment. In addition, this design feature of the present invention helps secure the expanded stent so that it does not move once it is implanted and furthermore, minimizes projections into the blood stream.

The invention generally includes a plurality of radially expandable loop elements which are relatively independent in their ability to expand and to flex relative to one another. The individual radially expandable elements of the stent are dimensioned to minimize the strut from twisting or rotating during expansion. Interconnecting elements or a backbone extends between the adjacent loop elements to provide increased stability and a preferable position for each loop to prevent warping of the stent upon the expansion thereof. The resulting stent structure is a series of radially expandable loop elements which are spaced longitudinally close enough so that the obstruction, vessel wall and any small dissections located at the treatment site of a body lumen may be dilated or pressed back into position against the lumenal wall.

The manufacturing process of the present invention utilizes optimized stress-strain curve characteristics to achieve, unlike other non-wire stent designs, improved mechanical properties throughout the stent. The optimized stress-strain curve of the materail increases both the yield strength and the ultimate tensile strength of the expanded stent, increasing its resistance to structural failure (fracture) or stent crushing.

12 Claims, 7 Drawing Sheets

U.S. PATENT DOCUMENTS

| | | |
|---|---|---|
| 5,019,090 A | 5/1991 | Pinchuk |
| 5,037,392 A | 8/1991 | Hillstead |
| 5,092,877 A | 3/1992 | Pinchuk |
| 5,102,417 A | 4/1992 | Palmaz |
| 5,104,404 A | 4/1992 | Wolff |
| 5,167,614 A | 12/1992 | Tessman |
| 5,192,297 A | 3/1993 | Hull |
| 5,192,307 A | 3/1993 | Wall |
| 5,195,984 A | 3/1993 | Schatz |
| 5,222,971 A | 6/1993 | Willard |
| 5,226,913 A | 7/1993 | Pinchuk |
| 5,266,073 A | 11/1993 | Wall |
| 5,282,823 A | 2/1994 | Schwartz |
| 5,304,200 A | 4/1994 | Spaulding |
| 5,306,294 A | 4/1994 | Winston |
| 5,354,308 A | 10/1994 | Simon |
| 5,395,390 A | 3/1995 | Simon |
| 5,397,355 A | 3/1995 | Marin |
| 5,405,377 A | 4/1995 | Cragg |
| 5,411,549 A | 5/1995 | Peters |
| 5,411,551 A | 5/1995 | Winston |
| 5,421,955 A | 6/1995 | Lau |
| 5,423,885 A | 6/1995 | Williams |
| 5,443,496 A | 8/1995 | Schwartz |
| 5,449,372 A | 9/1995 | Schmaltz |
| 5,449,373 A | 9/1995 | Pinchasik |
| 5,464,650 A | 11/1995 | Berg |
| 5,514,154 A | 5/1996 | Lau |
| 5,527,354 A * | 6/1996 | Fontaine et al. ................ 623/1 |
| 5,624,508 A | 4/1997 | Flomenblit |
| 5,769,883 A | 6/1998 | Buscemi et al. ................ 623/1 |
| 5,902,475 A * | 5/1999 | Trozera et al. ............... 205/655 |

* cited by examiner

STENT HAVING TAPERED STRUTS

This is a continuation-in-part application of co-pending U.S. patent application Ser. No. 08/835,015, filed on Apr. 8, 1997 and entitled "Method for Manufacturing a Stent." The contents of the application identified in this paragraph, are incorporated herein by reference.

FIELD OF THE INVENTION

In general, the present invention relates to percutaneous transluminal devices and methods which are used to treat obstructed (sclerotic) vessel lumina in humans. In particular, the present invention is an improved stent that requires low expansion pressure for deployment and improved embedding of the struts within the vessel wall.

BACKGROUND OF THE INVENTION

Cardiovascular disease is commonly accepted as being one of the most serious health risks facing our society today. Diseased and obstructed coronary arteries can restrict the flow of blood and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Conventional open heart surgery is, of course, very invasive and traumatic for patients undergoing such treatment. In many cases, less traumatic, alternative methods are available for treating cardiovascular disease percutaneously. These alternate treatment methods generally employ various types of balloons (angioplasty) or excising devices (atherectomy) to remodel or debulk diseased vessel segments. A further alternative treatment method involves percutaneous, intraluminal installation of one or more expandable, tubular stents or prostheses in sclerotic lesions. Intraluminal endovascular prosthetic grafting is an alternative to conventional vascular surgery. Intraluminal endovascular grafting involves the percutaneous insertion into a blood vessel of a tubular prosthetic graft and its delivery via a catheter to the desired location within the vascular system. The alternative approach to percutaneous revascularization is the surgical placement of vein, artery, or other by-pass segments from the aorta onto the coronary artery, requiring open heart surgery, and significant morbidity and mortality. Advantages of the percutaneous revascularization method over conventional vascular surgery include obviating the need for surgically exposing, removing, replacing, or by-passing the defective blood vessel, including heart-lung by-pass, opening the chest, and general anesthesia.

Stents or prostheses are known in the art as implants which function to maintain patency of a body lumen in humans and especially to such implants for use in blood vessels. They are typically formed from a cylindrical metal mesh which expand when internal pressure is applied. Alternatively, they can be formed of wire wrapped into a cylindrical shape. The present invention relates to an improved stent design which by its specifically configured struts can facilitate the deployment and embedment of the stent within a vessel and is constructed from a manufacturing process which provides a controlled and superior stress yield point and ultimate tensile characteristics.

Stents or prostheses can be used in a variety of tubular structures in the body including, but not limited to, arteries and veins, ureters, common bile ducts, and the like. Stents are used to expand a vascular lumen or to maintain its patency after angioplasty or atherectomy procedures, overlie an aortic dissecting aneurysm, tack dissections to the vessel wall, eliminate the risk of occlusion caused by flaps resulting from the intimal tears associated with primary interventional procedure, or prevent elastic recoil of the vessel.

Stents may be utilized after atherectomy, which excises plaque, cutting balloon angioplasty, which scores the arterial wall prior to dilatation, or standard balloon angioplasty to maintain acute and long-term patency of the vessel.

Stents may be utilized in by-pass grafts as well, to maintain vessel patency. Stents can also be used to reinforce collapsing structures in the respiratory, biliary, urological, and other tracts.

Further details of prior art stents can be found in U.S. Pat. No. 3,868,956 (Alfidi et. al.); U.S. Pat. No. 4,739,762 (Palmaz); U.S. Pat. No. 4,512,338 (Balko et. al.); U.S. Pat. No. 4,553,545 (Maass et. al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); U.S. Pat. No. 4,886,062 (Wiktor); U.S. Pat. No. 5,102,417 (Palmaz); U.S. Pat. No. 5,104,404 (Wolff); U.S. Pat. No. 5,192,307 (Wall); U.S. Pat. No. 5,195,984 (Schatz); U.S. Pat. No. 5,282,823 (Schwartz et. al.); U.S. Pat. No. 5,354,308 (Simon et. al.); U.S. Pat. No. 5,395,390 (Simon et. al), U.S. Pat. No. 5,421,955 (Lau et. al.); U.S. Pat. No. 5,443,496 (Schwartz et. al.); U.S. Pat. No. 5,449,373 (Pinchasik et. al.); U.S. Pat. No. 5,102,417 (Palmaz); U.S. Pat. No. 5,514,154 (Lau et. al); and U.S. Pat. No. 5,591,226 (Trerotola et. al.).

In general, it is an object of the present invention to provide a stent or prosthesis which can be readily expanded and embedded into an obstruction or vessel wall with low dilatation pressure thereby minimizing the trauma and damaged imparted to the vessel wall during deployment of the stent.

It is also an object of the present invention to utilize a specifically designed configuration of the outer strut surface to facilitate embedment of the stent structure into the obstruction and vessel wall with low dilatation pressure.

Another object of the present invention is to employ a manufacturing process which optimizes the stress-strain curve characteristics that achieves an increased yield strength and ultimate tensile strength when compared to the other non-wire prior art stents.

SUMMARY OF THE INVENTION

The present invention is directed to an expandable stent which is relatively flexible along its longitudinal axis to facilitate delivery through tortuous body lumens, but which is stiff and stable enough radially in an expanded condition to maintain the patency of a body lumen such as an artery when implanted therein. In addition, the struts of the present invention have a specific trapezoidal, triangular or reduced radii configuration projecting radially outward that functions to reduce the forces necessary to penetrate the vessel wall with the stent thereby minimizing trauma or damage imparted to the wall during deployment.

The invention generally includes a plurality of radially expandable loop elements which are relatively independent in their ability to expand and to flex relative to one another. The individual radially expandable elements of the stent (cross-section of a strut) are dimensioned such that the aspect ratio of the height to width minimizes twisting or rotation during expansion. Interconnecting elements or a backbone extends between the adjacent loop elements to provide increased stability and a preferable position for each loop to prevent warping of the stent upon the expansion thereof. The resulting stent structure is a series of radially expandable loop elements which are spaced longitudinally close enough so that the obstruction, vessel wall and any small dissections located at the treatment site of a body lumen may be dilated or pressed back into position against the lumenal wall. The outward projecting strut surface converges towards the terminal end and is configured in a trapezoidal, triangular or rounded shape to facilitate embedment of the strut into the vessel wall utilizing low dilatation pressure. The individual loop elements may bend relative to adjacent loop elements without significant deformation, cumulatively providing a stent which is flexible along its length and about its longitudinal axis but is still very stiff in the radial direction in order to resist collapse.

The presently preferred structure for the expandable loop elements which form the stent of the present invention are generally a circumferential undulating or alternating loop pattern which comprises one of the radially expandable cylindrical elements. The transverse cross-section of the undulating component of the loop element preferably has an aspect ratio of about one to one (base to height) thereby minimizing any tendency of the strut to twist when expanded. The open reticulated structure of the stent allows for a large portion of the vascular wall to be exposed to blood which can improve the healing and repair of any damaged vessel lining.

The radial expansion of the expandable cylinder deforms the undulating or alternating loop pattern thereof similar to changes in a waveform which result from decreasing the waveform's amplitude and the frequency. Preferably, the undulating or alternation patterns of the individual loop structures are in phase with each other in order to yield uniform expansion and inhibit any crimping along its length. The expandable cylindrical structures of the stent are plastically deformed when expanded so that the stent will remain in the expanded condition and therefore they must be sufficiently rigid when expanded to prevent the compression of the struts and therefore partial or total collapse of the stent after deployment. The manufacturing process of the present stent invention utilizes optimized stress-strain curve characteristics to achieve, unlike other non-wire stent designs, improved mechanical properties throughout the stent. The optimized stress-strain curve increases both the yield strength and the ultimate tensile strength of the expanded stent increasing its resistance to structural failure (fracture) or stent crushing. During expansion of the stent, the radially projecting trapezoidal, triangular or reduced radii configuration of the struts outer surface will penetrate the obstruction and vessel wall. Due to the reduced area of the outer surface, the struts are able to pierce an obstruction or the vessel wall with relative easy thereby resulting in minimal trauma or damage to the vessel wall. In addition, this design feature of the present invention helps secure the expanded stent so that it does not move once it is implanted and furthermore, minimizes projections into the blood stream.

The elongated elements which interconnects adjacent radially expandable elements should have a transverse cross-section similar to the transverse dimensions of the undulating or alternation loop components of the radially expandable element. The interconnecting elements preferably are not a unitary structure but rather alternates sectionally along the length at various degrees around the circumference of the stent. In an alternate embodiment, the interconnecting element is a unitary structure which resembles a backbone connecting the expandable loop elements.

In a presently preferred embodiment of the invention, the stent is conveniently and easily formed by first heat-treating the mechanically hardened tubular member to achieve optimum stress-strain characteristics e.g. yield strength, elongation and ultimate tensile strength. Then, the tubular member, comprising stainless steel, platinum, gold alloy, or a gold/platinum alloy, is electro-cleaned with an appropriate solution. Once the tubular member is cleansed of contaminates, the outer surface is uniformly coated with a photo-sensitive resist. Optionally, a coupling agent may be used to facilitate the bonding of the photosensitive resist to the tubular member. The coupling agent is not essential in that some tubular member compositions bond directly to the photo-sensitive resist solution without the need for a coupling agent.

This coated tubular member is then placed in an apparatus designed to rotate the tubular member while the coated tubular member is exposed to a designated pattern of ultraviolet (UV) light. The apparatus controls the exposure of the coated tubular member by utilizing a photographic film with a specified computer generated imprinted configuration, transferring the UV light in the specified pattern to the coated tubular member. The UV light activates the photo-sensitive resist causing the areas where UV light is present to expose (cross-link) the photo-sensitive resist. The photo-sensitive resist forms cross links where is it exposed to the UV light thus forming a pattern of hardened and cured polymer which mimics the particular stent design surrounded by uncured polymer. The film is adaptable to virtually an unlimited number of intricate stent designs. The process from the apparatus results in the tubular member having a discrete pattern of exposed photo-sensitive material with the remaining areas having unexposed photo-sensitive resist.

The exposed tubular member is immersed in a negative resist developer for a specified period of time. The developer removes the relatively soft, uncured photo-sensitive resist polymer and leaves behind the cured photo-sensitive resist which mimics the stent pattern. Thereafter, excess developer is removed from the tubular member by rinsing with an appropriate solvent. At this time, the entire tubular member is incubated for a specified period of time, allowing the remaining photo-sensitive resist polymer to fully cure and bond to the surface of the processed tubular member.

The processed tubular member is then exposed to a electrochemical etching process which removes uncovered metal from the tubular member, resulting in the final tubular member or stent configuration. Since the tubular member has not been subjected to any process such as additional heat treatments, welding/brazing or laser cutting, the finished stent will maintain the optimized stress-strain characteristics obtained in the initial heat-treatment process.

The stent embodying features of the invention can be readily delivered to the desired lumenal location by mounting it on an expandable member of a delivery catheter, for example, a balloon or mechanical dilatation device, and passing the catheter/stent assembly through the body lumen to the site of deployment.

Other features and advantages of the present invention will become more apparent from the following detailed description of the invention. When taken in conjunction with the accompanying exemplary drawings.

DETAILED DESCRIPTION OF THE PREFERRED EMBODIMENTS

Figure 1:
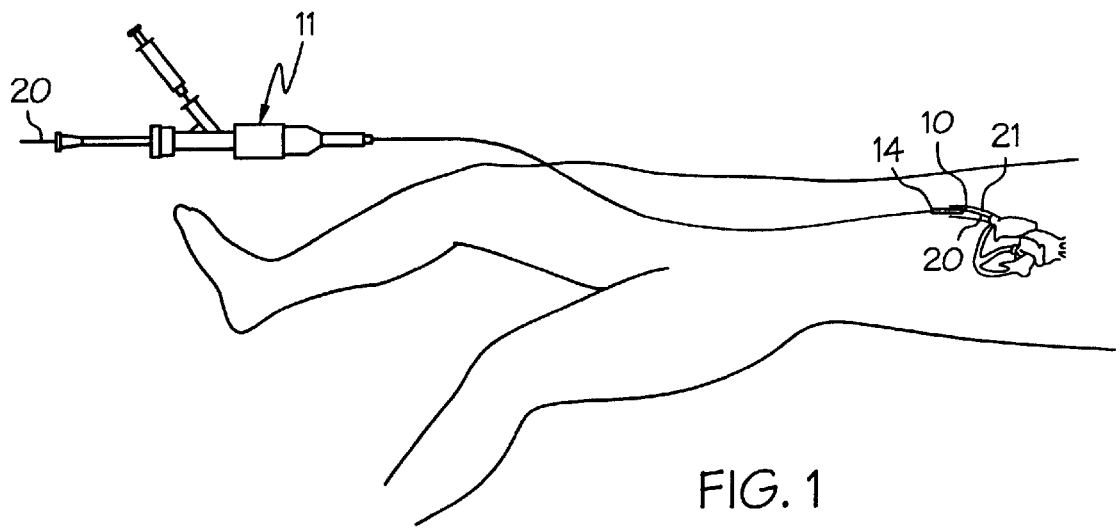
FIG. 1 is an elevational view of a stent embodying features of the invention which is mounted on a delivery catheter and disposed within an arterial segment.

FIG. 1 illustrates a stent 10 incorporating features of the invention which is mounted onto a delivery catheter 11 threaded over guidewire 20. The delivery catheter 11 has an expandable portion or balloon 14 for expanding of the stent 10 within an artery 21. The delivery catheter 11 onto which the stent 10 is mounted, is essentially the same as a conventional balloon dilatation catheter for angioplasty procedures or may consist of a mechanical dilatation device. The balloon 14 may be formed of suitable materials such as polyethylene, polyethylene terephthalate (PET) or polyethylene napthalate (PEN). In order for the stent 10 to remain stationary on the balloon 14 during delivery to the site of the obstruction within the artery 21, the stent 10 is generally collapsed onto the balloon.

Figure 2:
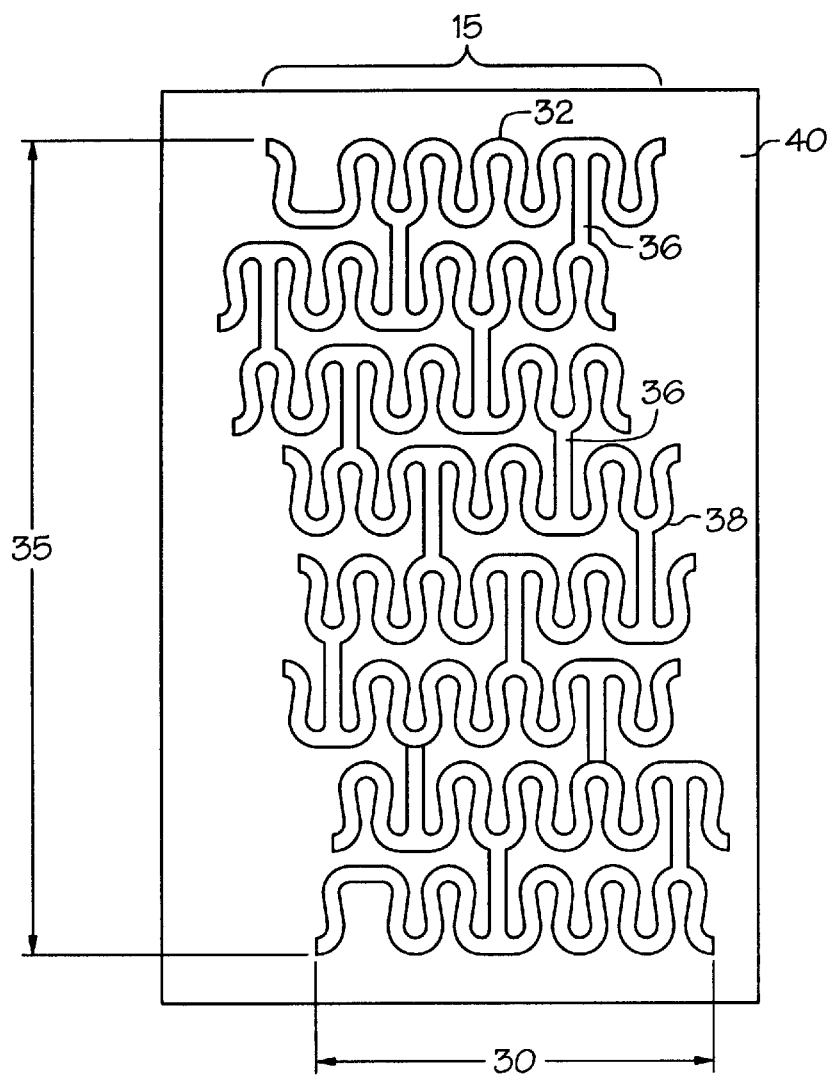
FIG. 2 is a plan view illustration of one frame of film with a stent configuration of the present invention imprinted on the film.
Figure 5:
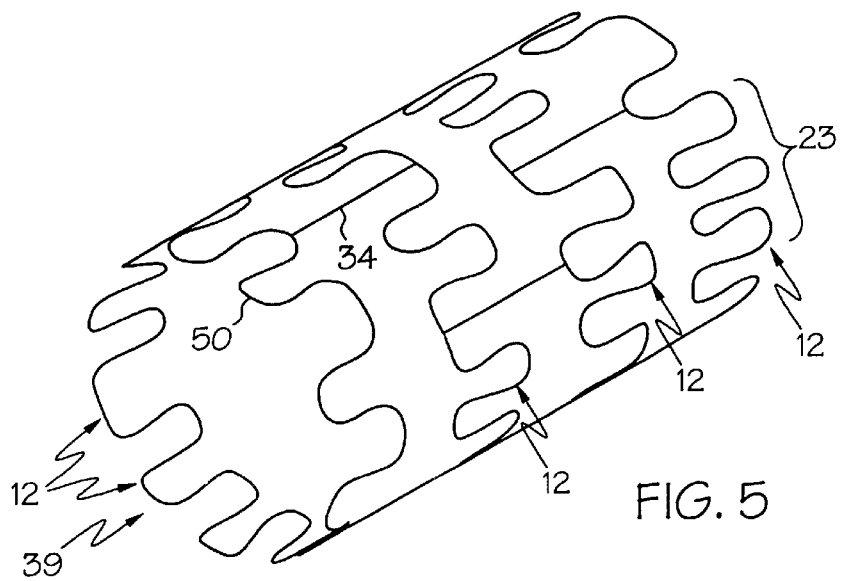
FIG. 5 is a perspective view of one stent configuration, showing the position and relationship of the loop or struts with the connecting elements.

FIG. 2 shows a preferred stent configuration imprinted on a transparent photographic film. The drawing of the pattern is generated on a computer program, reduced and printed onto a transparent film. For example, a mechanical drawing or stress analysis program can be used to develop the computer generated printouts. The printout is then sent to a film processing facility which reduces the printout and generates a precisely dimensioned negative. As discussed in more detail below, the dimensions of the negative must be calibrated to render a specific stent design. Because of regulations concerning patent drawings which prohibits large blackened areas, an explanation of the drawings used to represent the photographic film is necessary. In FIG. 2, the open (transparent) spaces 38 which allow the UV light to pass through the film are represented as solid black lines (with white cores) which comprise a series of alternating loops 15. The alternating loop of the film 32 create the struts 50 which circumferentially comprise the expandable cylindrical elements 12 of stent 10 as shown in FIG. 5. Similarly, the linear sections 36 connecting the alternating or undulating patterns comprise the interconnecting elements 32 of stent 10 (FIG. 5). The white areas 40 of the FIG. 2 represent the exposed (black) areas of the film which will block the UV light from passing through the film and exposing the underlying areas to UV. An example of a suitable film that can be employed in the present invention is Kodak ALI-4 Accumax film made by Kodak Industries. The length 30 of stent imprint is directly equal (1 to 1) to the circumference of present stent invention. The width 35 is equivalent to the working length of the processed stent.

Figure 3:
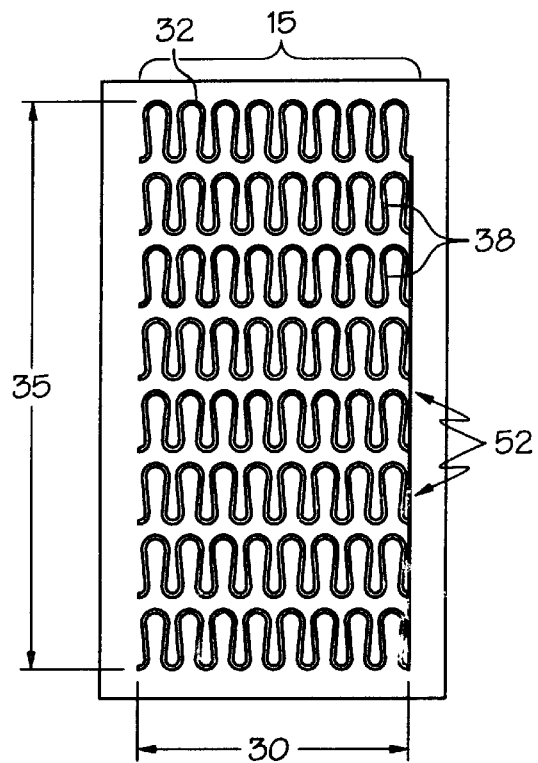
FIG. 3 is a plan view illustration of one frame of film with a stent configuration of another embodiment of the present invention imprinted on the film showing the single backbone connecting element.

FIG. 3 illustrates another embodiment of the present stent invention wherein linear section(s) 36 (which become the interconnecting elements) are disposed between alternating loops 32 (which become the radially expandable cylindrical elements) in different configurations. In FIG. 3, the resulting configuration of the stent from the imprinted film will have a single connection backbone 52. The single interconnecting element represents a backbone 52 connecting the radially expandable cylindrical elements 12 of stent 10. Not shown but contemplated in the present invention, the interconnecting elements 34 may be distributed 120 degrees around the circumference of the stent 10. Disposing three or more interconnecting elements 34 between adjacent radially expandable cylindrical elements 12 will generally give rise to the same considerations discussed above for the one and two interconnecting element designs.

Figure 4:
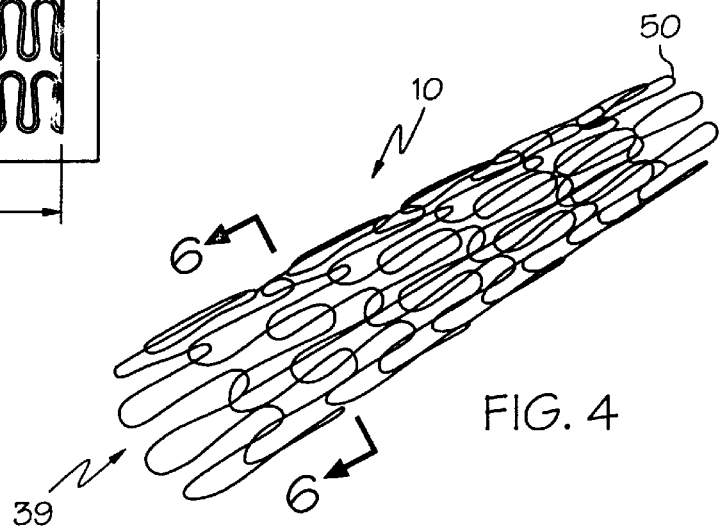
FIG. 4 is a perspective view of a entire stent embodying features of the invention in an unexpanded state.

FIGS. 4 and 5 are representations of the preferred stent design 10 that results from the photo and etch method and the embodiment shown in FIG. 2. The stent generally comprises a plurality of radially expandable cylindrical elements 12 disposed generally coaxially and interconnected by elements 34 disposed between adjacent expandable elements. The portion of the metal covered by the photoresist that was exposed to UV illumination and changed physical properties are retained during the electrochemical process and remain intact as the struts or loops 50 of stent 10. The portions of the photoresist that were not exposed to UV illumination are removed during the development stage. The exposed metal is then chemically dissolved by employing an electrochemical process that results in the open spaces 39 in the stent 10. The structure resulting from a pattern of loops or struts 50 and open spaces 39 comprises the desired stent configuration. In keeping with the invention, and with reference to FIGS. 4 and 5, radially expandable cylindrical elements 12 are in the form of a number of loop alterations or undulations 23 of the stent resembling a serpentine pattern. FIG. 4 also illustrates the stent design in which the radially expandable cylindrical elements 12 are in an undulating pattern but out of phase with adjacent expandable cylindrical elements.

FIG. 5 is an enlarged perspective view of the stent 10 shown in FIG. 4 with one end of the stent shown in an exploded view to illustrate in greater detail the placement of interconnecting elements 34 between adjacent radially expandable elements 12. Each pair of the interconnecting elements 34 on one side of an expandable element 12 are preferably placed to achieve maximum flexibility for a stent. In the embodiment shown in FIG. 5, stent 10 has two interconnecting elements 34 between adjacent radially expandable cylindrical elements 12 which are approximately 180 degrees apart. The next pair of interconnecting elements 13 on one side of a cylindrical element 12 are offset by ninety (90) degrees from the adjacent pair. The alternation of the interconnecting elements results in a stent which is longitudinally flexible in essentially all directions. Various configurations for the placement of interconnecting elements are possible and another example is illustrated schematically in FIG. 3. However all of the interconnecting elements of an individual stent should be secured to either the peaks or valleys of the alternating loop elements in order to prevent shortening of the stent during the expansion thereof and all of the radially facing struts will have one of the specifically designed configurations.

The pattern of FIGS. 4 and 5 can be formed of any size; a preferable size of stent 10 is between 0.035 thousandths to 0.100 thousandths in diameter when formed and in the constrained configuration. The expanded or deployed diameter of stent 10 ranges from 2.0 mm to 8.0 mm with a preferred range for coronary applications of 2.5 mm to 6.0 mm. The length of the stent 10 is virtually constant from its initial formation length to its length when expanded and ranges from 2 mm to 50 mm, with a preferred length for coronary applications of 5 mm to 20 mm.

Each radially expandable cylindrical element 12 of the stent 10 may be independently expanded. Therefore, the balloon 14 may be provided with an inflated shape other than cylindrical, e.g. tapered, to facilitate implantation of the stent 10 in a variety of body lumen shapes.

The particular pattern and how many undulations per unit of length around the circumference of the radially expandable cylindrical element 12, or the amplitude of the loops, are chosen to fill particular mechanical requirements for the stent such as expanded size and radial stiffness. The number of undulations may also be varied to accommodate placement of interconnecting elements 34 at the peaks of the undulations or along the sides of the undulations (not shown). As previously mentioned, each radially expandable cylindrical element 12 is connected by interconnecting elements 34. Undulating pattern 23 is made up of a plurality of U shaped alternating loops. Alternately, the undulating pattern could be made up of W-shaped members or Y-shaped members each having a different radius so that expansion forces are more evenly distributed over the various members.

Figure 9A:
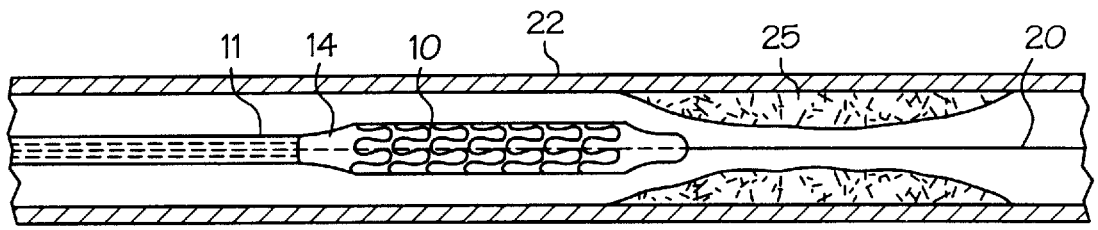
FIG. 9A is an elevational view, partially in section, similar to that shown in FIG. 1 wherein the stent is collapsed upon the delivery catheter within the arterial segment, and just proximal to a vascular obstruction.
Figure 9B:
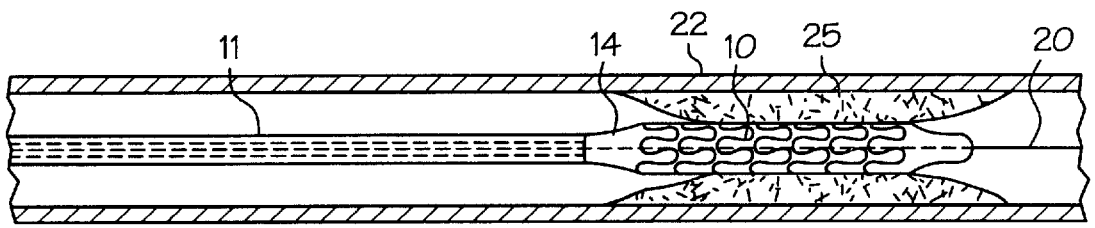
FIG. 9B is an elevational view, partially in section, similar to that shown in FIG. 1 wherein the stent, in its collapsed configuration, is positioned within the vascular obstruction.
Figure 9C:
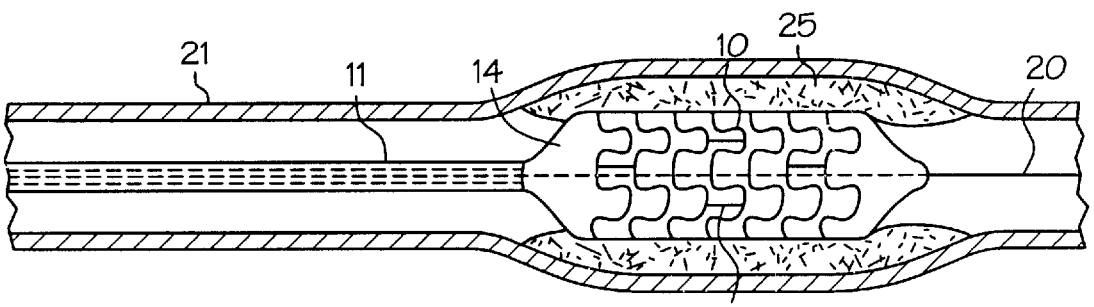
FIG. 9C is an elevational view, partially in section, similar to that shown in FIG. 1 wherein the stent is expanded within the vascular segment and embedding the specifically configured struts of the stent against and into the arterial wall.
Figure 9D:
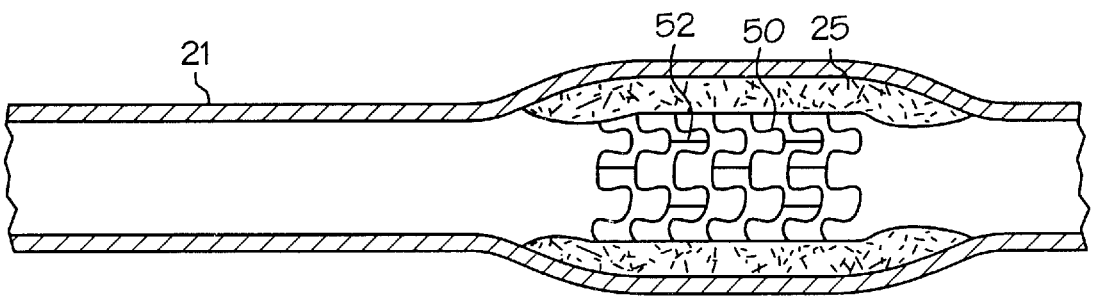
FIG. 9D is an elevational view, partially in section, similar to that shown in FIG. 1 wherein the delivery catheter has been withdrawn and the stent is fully deployed within the vascular segment.

The stent 10 serves to hold open the artery 21 after the catheter 11 is withdrawn, as illustrated by FIG. 9D. The undulating portion of the radially expandable sections 12 provide good tacking characteristics to prevent stent movement within the artery. Furthermore, the closely spaced radially expandable cylindrical elements 12 at regular intervals provide uniform support for the wall 22 of the artery 21, and consequently are well adapted to tack up and hold in place small flaps or dissections in the wall 22 of the artery 21.

Figure 6A:
FIG. 6A is a cross-sectional view of one configuration of the outer surface of a strut as seen along line 4—4 in FIG. 4 showing a trapezoidal protruding configuration that is directed radially from the longitudinal axis of the stent.
Figure 6B:
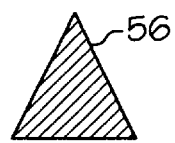
FIG. 6B is a cross-sectional view of another configuration of the outer surface of a strut as seen along line 4—4 in FIG. 4 showing a triangular protruding configuration that is directed radially from the longitudinal axis of the stent.
Figure 6C:
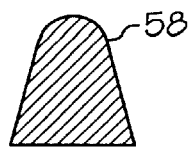
FIG. 6C is a cross-sectional view of another configuration of the outer surface of a strut as seen along line 4—4 in FIG. 4 showing a protrusion with a reduced radius that is directed radially from the longitudinal axis of the stent.

The method of manufacturing the present invention results in the preferred stent design 10 having specifically configured struts 50. FIGS. 6A, 6B, and 6C illustrate, in cross-section, three exemplary stent strut designs. As demonstrated in FIG. 6A, the preferred stent design has the outer portion of the struts protruding in a trapezoidal configuration 54 which is directed radially from the longitudinal axis of the stent. The pattern of the preferred stent employs cross-section FIG. 6A in a series of U-shaped loops 50 and an alternating connecting elements 34 running along the length of the stent, thereby forming the basic scaffold of the stent design.

In an alternate embodiment the pattern of stent 10 is similar to that of FIGS. 4, 5 and 6A but differs in the outer portion of the strut comprising a triangular configuration (FIG. 6B) where the point of the triangle is directed radially from the longitudinal axis of the stent. In an another alternate embodiment, the pattern of stent 10 is similar to that of FIGS. 4, 5 and 6A, but differs in the outer portion of the strut comprising an extended base with a reduced radius 58 (FIG. 6C) that is directed radially from the longitudinal axis of the stent.

Figure 7A:
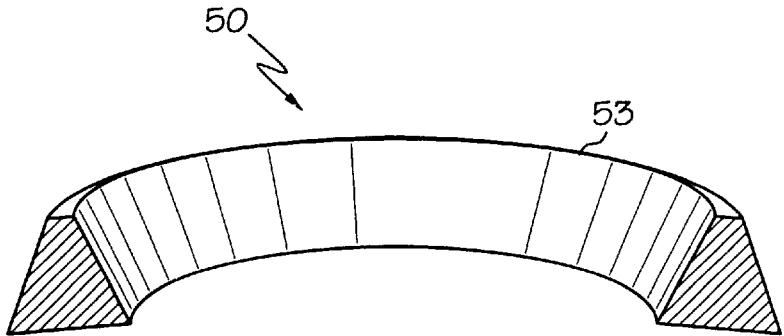
FIG. 7A is an enlarged partial view of one loop or strut of the stent of FIG. 4 showing a trapezoidal protruding configuration that is directed radially from the longitudinal axis of the stent.
Figure 7B:
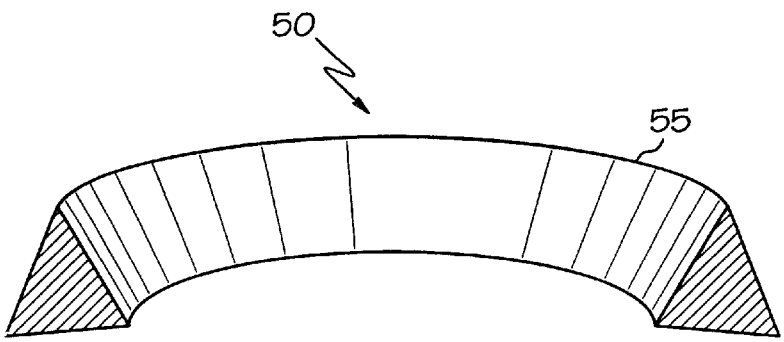
FIG. 7B is an enlarged partial view of one loop or strut of the stent of FIG. 4 showing a triangular protruding configuration that is directed radially from the longitudinal axis of the stent.
Figure 7C:
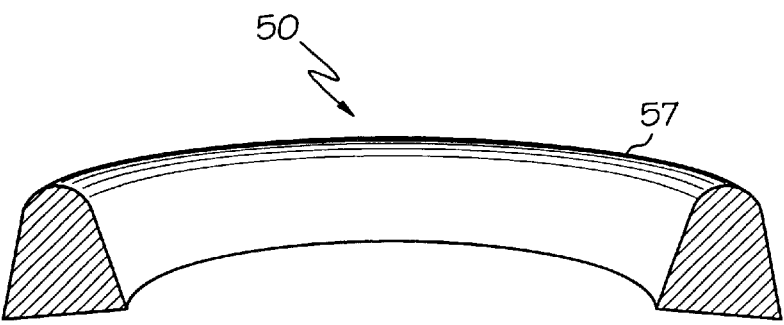
FIG. 7C is an enlarged partial view of one loop or strut of the stent of FIG. 4 showing a protrusion with a reduced radius that is directed radially from the longitudinal axis of the stent.

A terminal section of the loop of stent 10 is shown in FIGS. 7A, 7B, and 7C. It can be seen in the cross-sectional illustration that the strut has a trapezoidal configuration 53 in FIG. 7A, a triangular configuration 55 in FIG. 7B, and an outer reduced radius configuration 57 in FIG. 7C. Each strut configuration can be associated with any combination of alternating loops or struts 50 and interconnecting elements 34. Furthermore, it can be seen that the aspect radio of the height to width minimizes twisting or rotation during expansion.

Figure 7D:
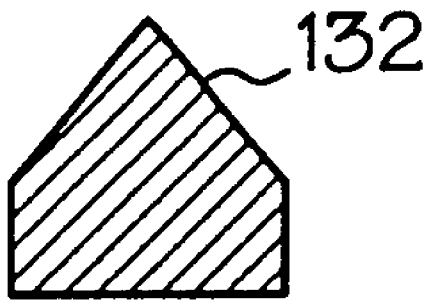
FIG. 7D is a cross-sectional view of another configuration of the loop elements having a trapezoidal protruding configuration.
Figure 7E:
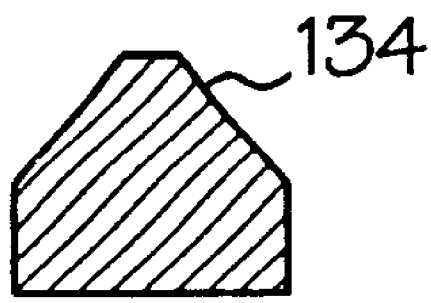
FIG. 7E is a cross-sectional view of another configuration of the loop elements having a triangular protruding configuration.

In another embodiment, as shown in FIG. 7D, the struts 132 have a cross-section which includes a trapezodial portion. In the embodiment of FIG. 7E, the struts 134 have a cross-section which includes a triangular portion.

Figure 8A:
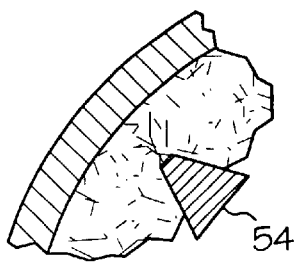
FIG. 8A is a cross-sectional view showing the trapezoidal configured strut scoring and penetrating an obstruction within in an arterial wall.
Figure 8B:
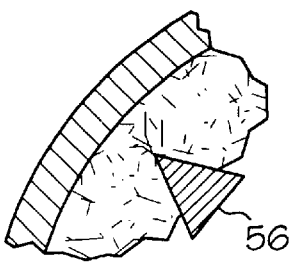
FIG. 8B is a cross-sectional view showing the triangular configured strut scoring and penetrating an obstruction within in an arterial wall.
Figure 8C:
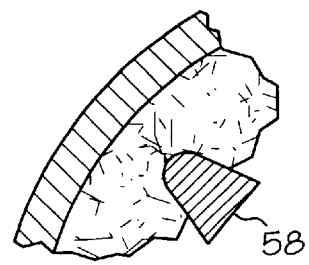
FIG. 8C is a cross-sectional view showing the reduced radius configured strut scoring and penetrating an obstruction within in an arterial wall.

As shown in FIGS. 8A, 8B and 8C, the specifically configured radially facing strut surfaces are designed to facilitate the embedment of the expanded stent into the arterial wall or obstruction. By providing a trapezoidal 54

(FIG. 8A), triangular 56 (FIG. 8B) or reduced radius 58 (FIG. 8C) configuration embedment of the stent is relatively atraumatic because less strut area is required to penetrate the vessel wall. Expansion and eventual embedment of the present invention stent is accomplished in such a way that vascular baropressure is overcome in a controlled and relatively docile manner. Vessel trauma and damage is thereby reduced resulting in less subsequent intimal or smooth muscle proliferation. In contrast, the prior art non-wire stents present a relatively flat surface to penetrate the vessel wall therefore providing none of the advantages described above for the present stent invention.

In a preferred embodiment, the delivery of the stent 10 is accomplished in the following manner. The stent 10 is first mounted onto an inflatable balloon 14 or mechanical delivery system (not shown) on the distal extremity of the delivery catheter 11. The stent 10 is crimped or collapsed to the exterior surface of balloon 14. The stent/catheter assembly is then introduced within the patient's vasculature through a guiding catheter utilizing the conventional Seldinger technique. A guidewire 20 is disposed across the obstruction within the vascular section and the stent/catheter assembly is advanced over a guidewire 20 to the obstruction (see FIG. 9A) Then the stent/catheter assembly is advanced further until the stent 10 is positioned and centered within the obstruction 25 (see FIG. 9B). The balloon 14 of the catheter is then inflated, expanding the stent 10 against the obstruction 25 and possibly arterial wall 22, as illustrated in FIG. 9C.

As shown in FIG. 9D, the artery 21 is preferably expanded slightly by the expansion of stent 10 to provide volume for the expanded lumen. As a result of this embedment, interference of blood flow by the stent is minimized as well as to prevent further movement. The radially expandable elements 12 (or struts 50) of stent 10 which are pressed into the wall of the artery 21 will eventually be covered with endothelial cell growth which further minimizes blood flow interference.

Figure 10:
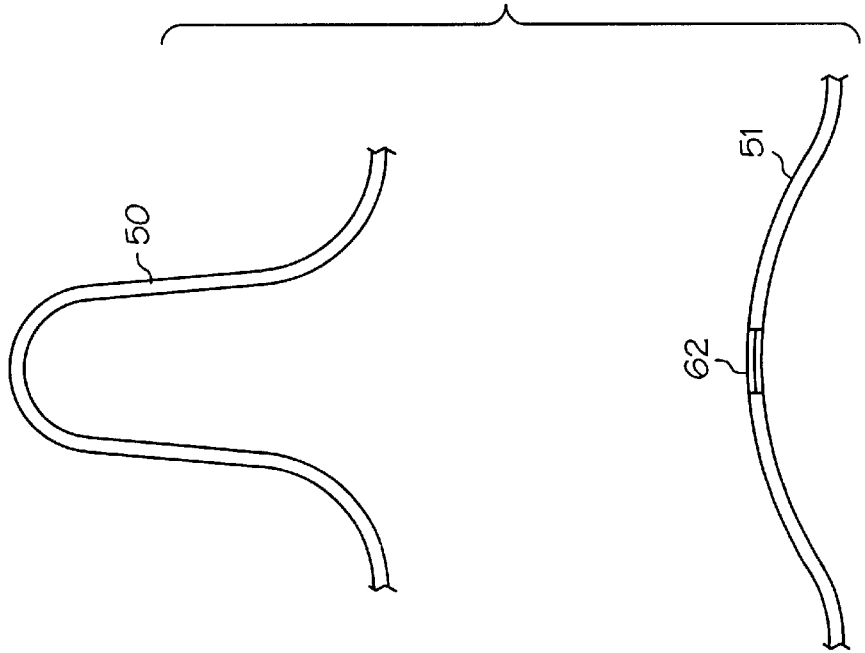
FIG. 10 is an illustration of a single strut or loop in both the unexpanded and expanded configurations demonstrating the amount of optimized stress-strain characteristics obtained upon deployment of prior art non-wire stents.

FIG. 10 illustrates the limited amount hardening (increased tensile loop or strength) that results when the prior art non-wire stents are plastically deformed during deployment. When the prior art non-wire strut 50 is expanded, a relatively small area 62 becomes hardened when deformed and therefore less resistance to crushing or further deformation.

Figure 11:
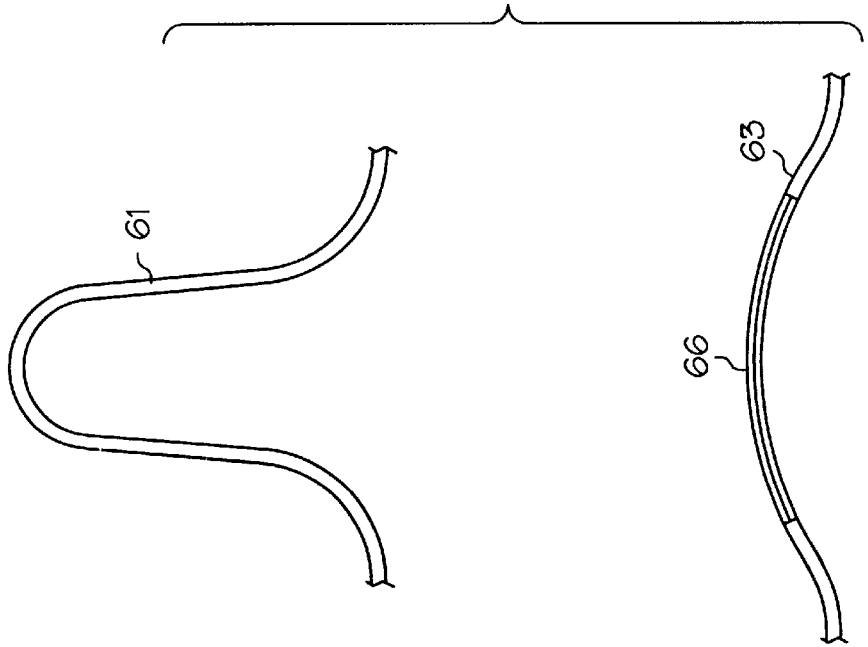
FIG. 11 is an illustration of a single strut or loop in both the unexpanded and expanded configurations demonstrating the amount of optimized stress-strain characteristics obtained upon deployment of the present invention stent.

FIG. 11 illustrates a large amount of hardening (increased tensile strength) that results when with the present invention is plastically deformed during deployment. The amount of cross sectional area having an increased tensile strength is achieved by the present invention's representative manufacturing processes and is substantially greater than for the non-wire prior art stents. As depicted in the upper and lower comparisons, as the loop or strut 61 is expanded, the center of the loop becomes hardened. Once the center becomes hardened, the adjacent areas on both sides of this hardened center become hardened as the plastic deformation continues. Due to the manufacturing process which optimizes the stress strain characteristics, when the loop is expanded to its fullest extent, the total area of hardening is significantly greater in the present invention than the prior art non-wire stents. The larger portion of hardening 66 equates to a stent having increased resistance to crushing and further deformation. Conversely, the prior art non-wire stents have a limited portion of hardening and therefore significantly less resistance to crushing or further deformation. This characteristic is clinically important, for any tendency of a stent to become crushed during deployment or worse yet, after deployed, could restrict blood flow or increase the potential for restenosis.

Figure 12:
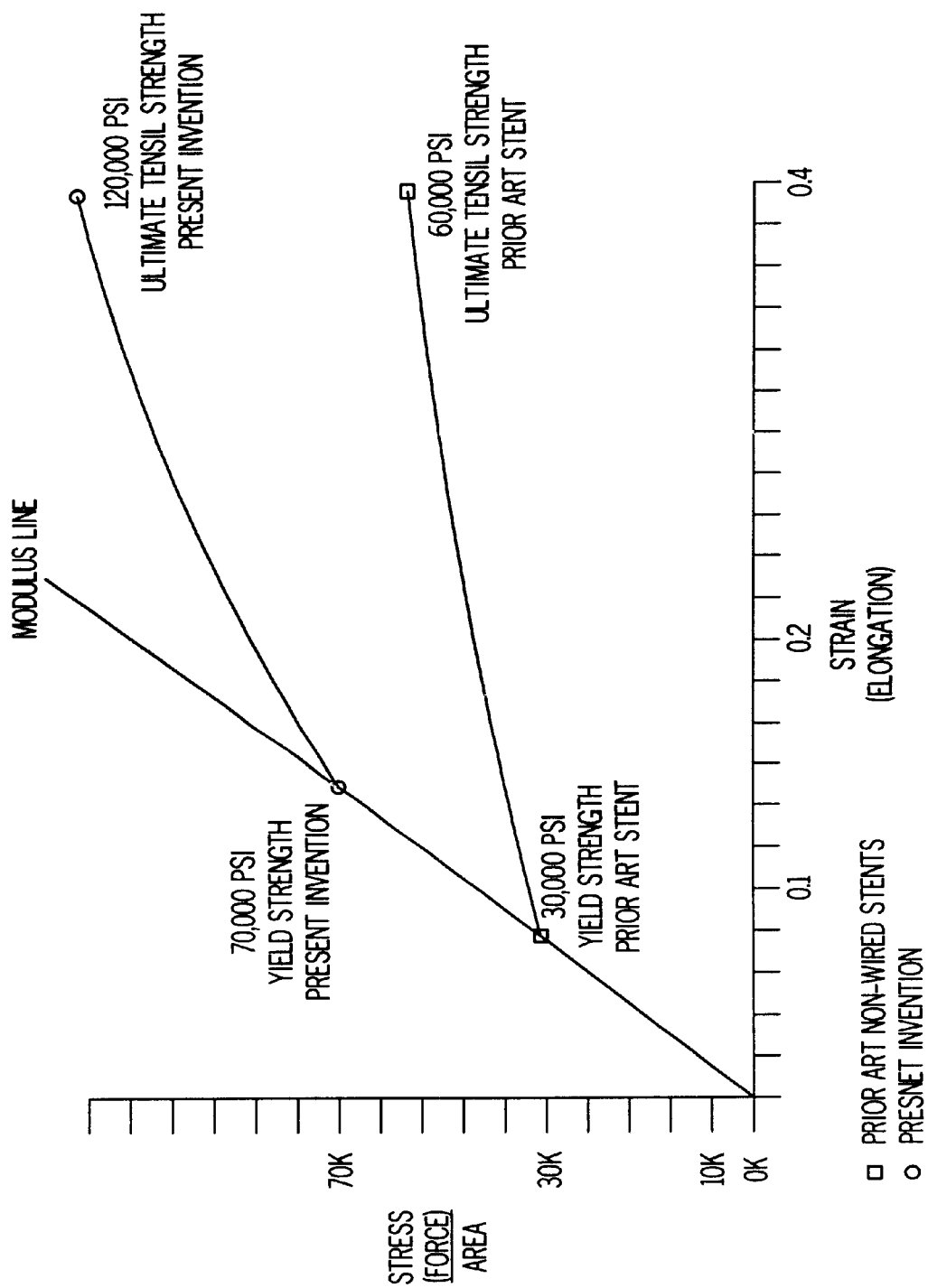
FIG. 12 is an representation of the stress-strain curve showing the relative ultimate tensile of the prior art stents versus the present invention stent.

FIG. 12 illustrates the a standard stress-strain chart comparing the curves for the prior art non-wire stents with the present stent invention. As the chart demonstrates, the prior art non-wire stents have an approximate 30,000 psi yield strength at which additional stain induces plastic deformation. The present invention can produce a yield strength ranging from 35,000 to 70,000 psi. The manufacturing process can select a yield point anywhere within this range to achieve the desired result. The higher end of the range is significantly greater than the prior art non-wire stents. These properties are responsible for the present invention having increased resistance to crushing.

Furthermore, FIG. 12 also demonstrates that the prior art non-wire stents have an ultimate tensile strength of approximately 60,000 psi. Any additional strain beyond this point results in failure of the material. The present invention can produce an ultimate tensile strength ranging from 65,000 to 120,000 psi. The manufacturing process can select a ultimate tensile strength anywhere within this range to achieve the desired result. The higher end of this range is significantly stronger then the prior art non-wire stents. These properties are responsible for the present invention also having an increased resistance to crushing.

While the invention has been illustrated and described herein in terms of its use as an intravascular stent, it will be apparent to those skilled in the art that the stent can be used in other instances such as to expand prostate urethras in cases of prostate hyperplasia. Other modifications and improvements may be made without departing from the scope of the invention.

Other modifications and improvements can be made to the invention without departing from the scope thereof:

I claim:

1. A stent having a flowpath therethrough for implanting in a vessel comprising:
    a plurality of loop elements which are independently expandable and which are interconnected to generally align said loop elements along a common longitudinal axis;
    one or more connecting elements for interconnecting said loop elements; and
    said loop elements comprising an inner surface facing the flowpath and an outer surface facing away from the flowpath, a first sidewall and a second sidewall, the first and second sidewalls converging toward one another in the direction of the outer surface, the loop elements having a cross-section which includes a substantially trapezoidal region, the substantially trapezoidal region extending inward from the outer surface toward the inner surface and bounded on two sides by the first and second sidewalls.

2. The stent of claim 1 wherein said loop elements or struts include an updulating, alternating loop or serpentine pattern.

3. A stent as recited in claim 1 wherein said loop elements are configured to be embedded into a vascular wall of a body lumen in order to more firmly attach said stent to said vascular wall.

4. A stent as recited in claim 1 wherein said loop elements are capable of maintaining their expanded condition upon expansion thereof.

5. A stent as recited in claim 1 wherein said stent is formed of a material selected from the group of materials consisting of stainless steel, platinum, gold alloy, and gold/platinum alloy.

6. The stent as recited in claim 1 further comprising a biocompatible coating.

7. The stent as recited in claim 1 wherein said loop elements have a yield strength greater than 35,000 psi.

8. The stent as recited in claim 1 wherein said loop elements have an ultimate tensile strength greater than 65,000 psi.

9. A stent for implanting in a vessel the stent having an inner surface and an outer surface, the stent having a flowpath therethough, the stent comprising:

a plurality of loop elements which are independently expandable and which are interconnected to generally align said loop elements along a common longitudinal axis; one or more connecting elements or interconnecting said loop elements; and said loop elements having a cross-section which is substantially trapezoidal wherein the cross-section widens from the outer surface to the inner surface.

10. A stent having an outer surface for supporting a vessel wall, said stent defining a longitudinal axis and comprising:

a plurality of generally annular shaped elements, each said element being centered around said axis each annular shaped element having a cross-section which is substantially trapezoidal in shape and which tapers toward the outer surface of the stent; and at least one connector holding said plurality of elements in a predetermined configuration along said axis.

11. A stent to support a vessel wall, said stent defining a longitudinal axis and comprising:

a plurality of annular shaped elements, said elements being a component of said stent and having a first surface and a second surface with said first surface of said element facing inwardly toward said axis and said second surface facing outwardly from said axis, said second surface of said elements having a lesser surface area than said first surface of said elements, wherein the annular shaped elements have a cross-section which is substantially trapezodial in shape.

12. A stent for implantation in a vessel of a living body formed by a wall having a lumen therein comprising a cylindrical wall having a circumference and defining a flow passage extending therethrough, said cylindrical wall having inner and outer surfaces and being perforate, said cylindrical wall being comprised of a plurality of spaced apart circumferential elements extending around the circumference and having a plurality spaced apart convolutions therein and at least one longitudinally extending element interconnecting said circumferential elements to provide a unitary cylindrical wall, at least certain of said elements of being formed with substantially trapezodial cross sections with inner cross sectional surfaces having first widths, said inner cross sectional surfaces being substantially flat and forming at least a part of the inner surface of the cylindrical wall and outer cross sectional surfaces having second widths, said outer cross sectional surfaces forming at least part of the outer surfaces of the cylindrical wall, said outer cross sectional surfaces having second widths which are substantially less than the first widths of the inner cross sectional surfaces, said at least certain of said elements having first and second substantially planar inclined surfaces disposed between the inner cross sectional surfaces and the outer cross sectional surfaces, said cylindrical wall being radially expandable in the lumen of the vessel into engagement with the wall of the vessel whereby the outer cross sectional surfaces of the cylindrical wall are embedded in the wall of the vessel to retain the stent in the desired position in the vessel.

* * * * *

UNITED STATES PATENT AND TRADEMARK OFFICE
CERTIFICATE OF CORRECTION

PATENT NO. : 6,475,233 B2  Page 1 of 1
APPLICATION NO. : 08/956672
DATED : November 5, 2002
INVENTOR(S) : Thomas Trozera It is certified that error appears in the above-identified patent and that said Letters Patent is hereby corrected as shown below:

Page 14 of the Issued Patent: Column 10, Line 53, delete "updulating" and insert --undulating--;
Page 15 of the Issued Patent: Column 11, Line 6, after the word "vessel" insert --,--;
Page 15 of the Issued Patent: Column 11, Line 12, delete second occurrence of "or" and insert --for--;
Page 15 of the Issued Patent: Column 11, Line 20, after the word "axis" insert --,--;
Page 15 of the Issued Patent: Column 11, Line 24, after the word "connector" insert --for--;
Page 15 of the Issued Patent: Column 12, Line 2, delete "trapezodial" and insert --trapezoidal--;
Page 15 of the Issued Patent: Column 12, Line 14, delete "trapezodial" and insert --trapezoidal--;

Signed and Sealed this

Twentieth Day of February, 2007

JON W. DUDAS
*Director of the United States Patent and Trademark Office*